US00PP23719P3

(12) United States Plant Patent
Bradford

(10) Patent No.: US PP23,719 P3
(45) Date of Patent: Jul. 9, 2013

(54) INTERSPECIFIC TREE NAMED 'PLUMRED IX'

(50) Latin Name: ***Prunus* sp.**
Varietal Denomination: Plumred IX

(76) Inventor: Lowell Glen Bradford, Le Grand, CA (US)

( * ) Notice: Subject to any disclaimer, the term of this patent is extended or adjusted under 35 U.S.C. 154(b) by 68 days.

(21) Appl. No.: 13/374,025

(22) Filed: Dec. 8, 2011

(65) Prior Publication Data

US 2013/0152247 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,220 P2 10/2003 Bradford

*Primary Examiner* — Annette Para

(57) ABSTRACT

The present invention relates to an interspecific tree and more particularly to a new and distinct variety broadly characterized by a medium size, moderately vigorous, hardy, and productive tree. Being self-unfruitful, the present variety requires cross pollination from an apricot, interspecific, or plum that blooms during the mid to late season. The present variety produces a very good bloom with an average amount of pollen to entice good bee activity to facilitate pollination. The fruit matures under the ecological conditions described during the last part of August, with first picking on Aug. 29, 2011, and will hang on the tree an additional twenty-five days. The fruit is uniformly medium in size, full red in skin color, clingstone in type, globose to oblate in shape, red to pink in flesh color, firm in texture, and excellent in flavor.

1 Drawing Sheet

Botanical classification: *Prunus* sp.
Varietal denomination: 'PLUMRED IX'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'Plumred IX'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2004 one such house containing a 'September Yummy®' plum tree (U.S. Plant Pat. No. 14,220) was crossed by me in this manner. To pollinate this plum tree, I selected bouquets from several sources of apricot and interspecific hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2007 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'September Yummy' plum (U.S. Plant Pat. No. 14,220), by being self-unfruitful and by producing fruit that ripens in the late season, that is somewhat crack resistant, and that is full red in skin color, but is distinguished therefrom by producing fruit that is full red to pink in flesh color, that is sweeter in flavor, somewhat smaller in size, and that matures about ten days earlier.

SUMMARY OF VARIETY

The present interspecific variety is characterized by a medium size, moderately vigorous, hardy, and productive tree. Being self-unfruitful, the present variety requires cross pollination from an apricot, interspecific, or plum that blooms during the mid to late season. The present variety produces a very good bloom with an average amount of pollen to entice good bee activity to facilitate pollination. The fruit matures under the ecological conditions described during the last part of August, with first picking on Aug. 29, 2011, and will hang on the tree an additional twenty-five days. The fruit is uniformly medium in size, full red in skin color, clingstone in type, globose to oblate in shape, red to pink in flesh color, firm in texture, and excellent in flavor.

DRAWING

The accompanying photograph consists of four whole fruits positioned to display the characteristics of the skin color and form, two half fruits divided to reveal the flesh and stone, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the firm ripe on Sep. 5, 2011, on the original tree during its seventh growing season. The flower and bud descriptions were developed during the previous blooming season. All major color code designations are by reference to the Inter-Society Color Council, National Bureau of Standards. Common color names are also used occasionally.

PARENTAGE

Seed parent: 'September Yummy®' (U.S. Plant Pat. No. 14,220).

Pollen parent: Unknown.

TREE

Size: Medium, reaching a height of 10' [3.05 m.] and a spread of 7' [2.13 m.] after seven growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Upright and Dense.

Form: Pruned to a Parallel "V".

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable mid to late seasonal blooming apricot, interspecific, or plum, such as 'Plumsweet IV' (U.S. Plant Pat. No. 16,461) interspecific tree.

Bearing: Regular bearer, with no crop failures observed, weather dependent.

Trunk:

- *Size*.—Medium, reaching a maximum diameter of 4" [101.6 mm.] after the seventh growing season.
- *Texture*.—Shaggy.
- *Bark color*.—A Dark grayish brown [62. d.gy.Br] and Grayish brown [61. gy.Br] variegation with Light yellowish brown [76. l.yBr] crevices present.
- *Lenticels*.—Approximate Number Per Square Inch: 12. Color: Light yellowish brown [76. l.yBr]. Size: ⅛" [3.2 mm.] to 7/16" [11.1 mm.]. Shape: Elongated, eye-shaped.

Branches:

- *Size*.—Diameter of the main scaffold is 2⅛" [54 mm.] measured 12" above the crotch, limb diameter measured 12" above first fork is 1¼" [31.8 mm.].
- *Texture*.—Smooth on first year wood, increasing roughness with age.
- *Color*.—1st Year Wood Topside: Grayish red [19. gy.R]. 1st Year Wood Underside: Brilliant yellow green [116. brill.YG]. 2nd Year Wood: Strong brown [55. s.Br].
- *Lenticels*.—Number Per Square Inch: About 40 on second year wood. Color: Light yellowish brown [76. l.yBr]. Size: 1/64" [0.4 mm.] to 1/16" [1.6 mm.]. Shape: Eye-shaped, elongated.

Leaves:

- *Size*.—Medium. Average Length: 3¼" [82.6 mm.]. Average Width: 1½" [38.1 mm.].
- *Arrangement*.—Alternate.
- *Thickness*.—Medium.
- *Form*.—Elliptical.
- *Apex*.—Acuminate.
- *Base*.—Acute with an average angle base angle of 60 degrees.
- *Surface*.—Smooth.
- *Color*.—Dorsal Surface: Moderate olive green [125. m.OlG]. Ventral Surface: Deep yellow green [118. deep YG].
- *Margin*.—Finely serrate.
- *Venation*.—Pinnately net veined.
- *Petiole*.—Average Length: ½" [12.7 mm.]. Average Thickness: 1/16" [1.6 mm.]. Color: Light yellow green [119. l.YG], often Deep red [13. deep R] where exposed to direct sunlight.
- *Stipules*.—Number: 2 per leaf at the young stage, up to 6 per growing tip. Average Length: ¼" [6.4 mm.]. Color: Light yellow green [119. l.YG] becoming Brilliant yellow green [116. brill.YG] with age.
- *Glands*.—Number: Usually 4 to 6 per leaf. Position: Usually opposite, positioned near the intersection of the petiole and the leaf blade. Size: Small. Form: Globose. Color: Brilliant yellow green [116. brill.YG] becoming Dark olive green [126. d.OlG] with age. Leaf buds: Pointed, medium.

Flower buds:

- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.

- *Average flower diameter*.—⅞" [22.2 mm.].
- *Number of petals*.—Five, no double blossoms observed.
- *Petal shape*.—Oval to circular.
- *Petal margin*.—Entire, slightly wavy.
- *Average petal diameter*.—7/16" [11.1 mm.].
- *Average petal length*.—9/16" [14.3 mm.].
- *Petal apex*.—Rounded.
- *Petal base*.—Obtuse.
- *Petal color*.—White [263. White] on both sides.
- *Anther color*.—Brilliant yellow [83. brill.Y].
- *Stigma color*.—Light greenish yellow [101. l.gY].
- *Sepal color*.—Light yellow green [119. l.YG] on the outer surface.
- *Sepal length*.—3/16" [4.8 mm.].
- *Sepal width*.—5/32" [4.0 mm.].
- *Sepal apex*.—Rounded to elliptical to match the width and length.
- *Sepal margin*.—Fairly smooth to the naked eye, slightly serrated when magnified.

*Average pistil length.*—½" [12.7 mm.].
*Average stamen length.*—7/16" [11.1 mm.].
*Fragrance.*—Moderate.
*Pollen production.*—Moderate, average bee enticement.
*Blooming period.*—Medium to late, with 'Santa Rosa' plum (unpatented).
*Onset of bloom.*—One percent on Mar. 4, 2011.
*Date of full bloom.*—Mar. 10, 2011.
*Duration of bloom.*—One to two weeks, dependent on ambient temperature.
*Bloom density.*—Moderate.
*Number per cluster.*—2 to 8, mostly 2.

FRUIT

Maturity when described: Firm ripe, Sep. 5, 2011.
Date of first picking: Aug. 29, 2011.
Date of last picking: Sep. 23, 2011.
Size: Uniform, Medium.
*Average diameter axially.*—2 5/16" [58.8 mm.].
*Average diameter across cheek plane.*—2 7/16" [61.9 mm.].
*Average diameter across suture plane.*—2⅜" [60.3 mm.].
*Typical weight.*—4.3 ounces [122 grams].
Form: Globose to somewhat oblate, symmetrical.
*Longitudinal section form.*—Round to oblate.
*Transverse section through diameter.*—Round.
Suture: An inconspicuous line located in a medium groove extending from the base to the pistil point.
Ventral surface: Rounded, lipped toward base.
Lips: Equal.
Cavity: Flaring, circular in suture plane, suture showing on one side.
*Depth.*—⅜" [9.5 mm.].
*Breadth.*—¾" [19.1 mm.].
Base: Somewhat truncate, slightly cordate if viewed parallel to the suture.
Apex: Rounded to somewhat truncate.
Pistil point: An inconspicuous Light yellowish green [135. l.yG] dot.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Slight.
*Tendency to crack.*—None observed in dry seasons.
*Color.*—Very deep red [14. v.deep R] over a Dark red [16. d.R] background with Light orange yellow [70. l.OY] freckling throughout.
*Bloom.*—Moderate.
Flesh:
*Color.*—Light yellowish pink [28. l.yPk] toward the stone, Deep red [13. deep R] toward the skin.
*Surface of pit cavity.*—Covered with Moderate red [15. m.R] broken fibers when twisted away from stone.
*Amygdalin.*—Moderate.
*Juice.*—Moderate, rich.
*Texture.*—Firm, crisp, meaty.
*Fibers.*—Few, fine, tender.
*Ripens.*—Somewhat earliest at apex.
*Flavor.*—A tasty balance of acid and sugar, typically 22 brix.
*Aroma.*—Moderate.
*Eating quality.*—Excellent.

STONE

Type: Clingstone.
Form: Oval.
Hilum: Narrow, oval.
Base: Acute, slightly oblique.
Apex: Acuminate.
Sides: Equal.
Surface: Fairly smooth with rounded ridges toward the base.
External color of stone: Strong brown [55. s.Br] when first removed.
Pit wall color when cracked: Light brown [57. l.Br].
Cavity surface color: Deep orange yellow [69. deep OY].
Average pit wall thickness: 1/16" [1.6 mm.].
Average width: 9/16" [14.3 mm.].
Average length: ⅞" [22.2 mm.].
Average breadth: ⅜" [9.5 mm.].
Tendency to split: None observed.
Kernel:
*Form.*—Oval.
*Skin color.*—Dark grayish yellow [91. d.gy.Y] when first removed.
*Pellicle color.*—Moderate olive brown [95. m.OlBr].
*Vein color.*—Moderate olive brown [95. m.OlBr].
*Taste.*—Bitter.
*Viable.*—Yes.
*Average width.*—⅜" [9.5 mm.].
*Average length.*—9/16" [14.3 mm.].
*Amygdalin.*—Scant.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its seed parent, 'September Yummy' plum (U.S. Plant Pat. No. 14,220), by being self-unfruitful and by producing fruit that ripens in the late season, that is somewhat crack resistant, and that is full red in skin color, but is distinguished therefrom by producing fruit that is full red to pink in flesh color, that is sweeter in flavor, somewhat smaller in size, and that matures about ten days earlier.

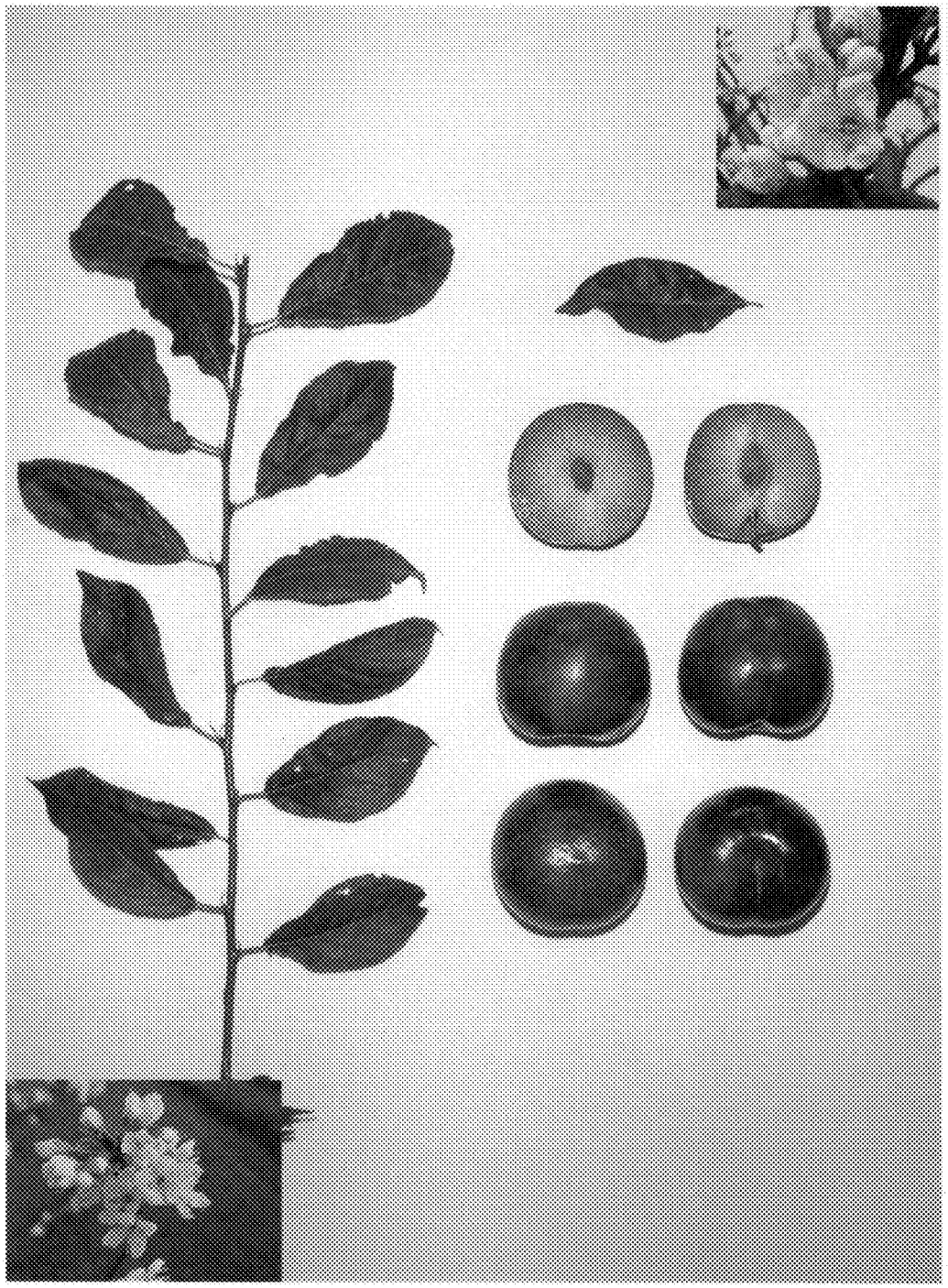

* * * * *